United States Patent
Moingeon et al.

(10) Patent No.: US 9,795,644 B2
(45) Date of Patent: Oct. 24, 2017

(54) REDUCTION OF IN VITRO GENOTOXICITY OF POLLEN EXTRACTS BY REMOVAL OF FLAVONOIDS

(75) Inventors: Philippe Moingeon, Verrieres le Buisson (FR); Thierry Batard, Versailles (FR); Bertrand Villet, Chatenay Malabry (FR)

(73) Assignee: STALLERGENES, Antony (FR)

( * ) Notice: Subject to any disclaimer, the term of this patent is extended or adjusted under 35 U.S.C. 154(b) by 8 days.

(21) Appl. No.: 13/376,238

(22) PCT Filed: Jun. 7, 2010

(86) PCT No.: PCT/EP2010/057935
§ 371 (c)(1),
(2), (4) Date: Feb. 24, 2012

(87) PCT Pub. No.: WO2010/139809
PCT Pub. Date: Dec. 9, 2010

(65) Prior Publication Data
US 2012/0148626 A1 Jun. 14, 2012

(30) Foreign Application Priority Data

Jun. 5, 2009 (EP) .................................. 09305517
Oct. 29, 2009 (EP) .................................. 09174479

(51) Int. Cl.
| | |
|---|---|
| A23J 1/00 | (2006.01) |
| A61K 39/35 | (2006.01) |
| A61K 39/36 | (2006.01) |
| C07K 1/00 | (2006.01) |
| C07K 14/00 | (2006.01) |
| C07K 16/00 | (2006.01) |
| C07K 17/00 | (2006.01) |
| A61K 36/00 | (2006.01) |

(52) U.S. Cl.
CPC .............. *A61K 36/00* (2013.01); *A61K 39/36* (2013.01)

(58) Field of Classification Search
None
See application file for complete search history.

(56) References Cited

U.S. PATENT DOCUMENTS

| | | | | |
|---|---|---|---|---|
| 4,234,569 | A * | 11/1980 | Marsh | ......................... 424/275.1 |
| 5,770,698 | A | 6/1998 | Berrens | |
| 6,297,426 | B1 * | 10/2001 | Albertsen et al. | ............ 800/278 |
| 2009/0162403 | A1 * | 6/2009 | Jacobi et al. | .............. 424/276.1 |

FOREIGN PATENT DOCUMENTS

WO WO 2004/009575 1/2004

OTHER PUBLICATIONS

Houp et al. 'Ultrafiltration and Diafiltration.' J. Validation Technology 40-45, Autumn 2009.*
Jutel et al., "Allergen-specific immunotherapy with recombinant grass pollen allergens," *J. Allergy Clin. Immunol.*, 116(3): 608-613 (2005).
Pajno et al., "Sublingual Immunotherapy: The Optimism and the Issues," *J. Allergy Clin. Immunol.*, 119(4): 796-801 (2007).
Int'l Search Report and Written Opinion issued in PCT/EP2010/057935 (2010).
Hidvegi et al., "Comparative study of the complement-activating and specific IgE-binding properties of ragweed pollen allergen" Clin Ex Immunol, 108:122-127 (1997).
Yoshitama et al "Flavonoids and Steroid Saponins in Trillium species," Abstracts: XVI International Botanical Congress, St. Louis, MO, USA, Aug. 1-7, 1999, Abstract No. 2129 (1999).
Middleton et al., "The Effects of Plant Flavonoids on Mammalian Cells: Implications for Inflammation, Heart Disease, and Cancer," Pharmacol. Rev., vol. 52, pp. 673-751 (2000).
Liu et al., "Effects of total alkaloids of Tripterygium hypoglaucum Hutch on tk gene of mouse lymphoma cells," Zhongguo Zhong Yao Za Zhi., 28:957-961 (2003)—English Abstract Only.
Antognoni et al.,"In Vitro Pollen Tube Growth Reveals the Cytotoxic Potential of the Flavonols, Quercetin and Rutin," ATLA 32:79-90 (2004).
Mo et al., "Biochemical complementation of chalcone synthase mutants defines a role for flavonols in functional pollen," Proc. Natl. Acad. Sci 89:7213-7217 (1992).
Campos et al., "The Unique Occurrence of the Flavone Aglycone Tricetin in Myrtaceae Pollen," Z. Naturforsch 57c, 944-946 (2002).
Gil et al., "Effect of Modified Atmosphere Packaging on the Flavonoids and Vitamin C Content of Minimally Processed Swiss Chard (Beta vulgaris Subspecies cycla)," J. Agric. Food Chem. 46:2007-2012 (1998).
D'Arcy, "Antioxidants in Australian Floral Honeys—Identification of health-enhancing nutrient components" Australian Government: Rural Industries Research and Development Corporation, Barton, AU, RIRDC Publication No. 05/040, pp. i-x and 1-84 (2005).
Moller et al., "Genotoxicity Induced by Furocoumarin Hydroperoxides in Mammalian Cells Upon UVA Irradiation," Biochemical and Biophysical Research Communications, pp. 216(2): 693-701 (1995).
Caria et al., "Genotoxicity of quercetin in the micronucleus assay in mouse bone marrow erythrocytes, human lymphocytes, V79 cell line and identification of kinetochore-containing (CREST staining) micronuclei in human lymphocytes," Mutation Research, 343:85-94 (1995).

(Continued)

*Primary Examiner* — Nora Rooney
(74) *Attorney, Agent, or Firm* — Browdy and Neimark, PLLC

(57) ABSTRACT

The invention relates to grass pollen extracts containing reduced amount of flavonoid glycosides in order to minimize the risks of genotoxicity of the grass pollen extracts. The invention also relates to a method of preparing grass pollen extracts containing reduced amount of flavonoid glycosides by ultrafiltration. Flavonoid glycosides are naturally present in grass pollen extracts and they have been identified as being responsible for the formation of flavonoid aglycones, which are genotoxic in vitro, under the influence of enzymes contained in the grass pollen extracts.

8 Claims, 2 Drawing Sheets

(56) References Cited

OTHER PUBLICATIONS

Figure 1:
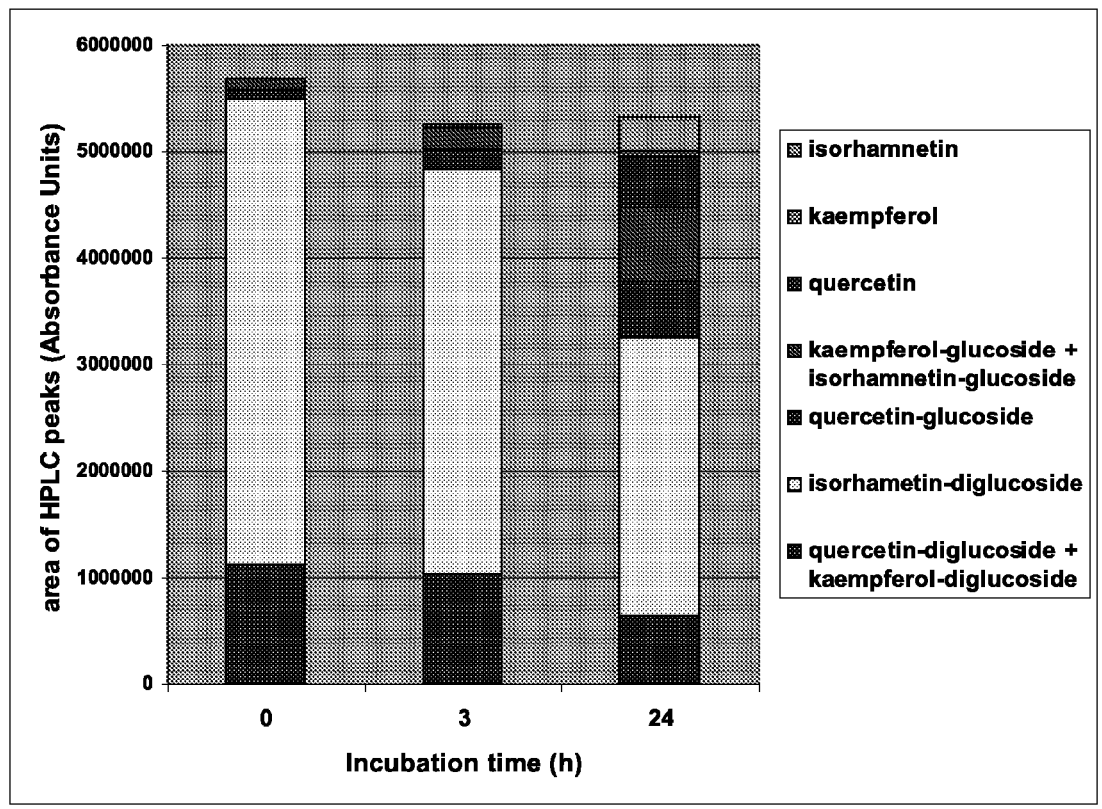

Muller et al., "Human biological relevance and the use of threshold-arguments in regulatory genotoxicity assessment: experience with pharmaceuticals," Mutation Research 464: 19-34 (2000).
Brown, J.P., "A Review of the Genetic Effects of Naturally Occurring Flavonoids, Anthraquinones and Related Compounds," Mutation Research, 75 (1980) 243-277 (1980).
Fung et al., " Mutagenic activity of some coffee flavor ingredients," Mutation Research 204:219-228 (1988).
G.E.Inglett., "Structure of a Grass Pollen Flavonoid Glycoside," Nature, 178:1346 (1956).
G.E. Inglett.,"Structure of Dactylin," J. Org. Chem, 22:189-192 (1957).
Kevekordes et al., "Micronucleus Formation in Human Lymphocytes and in the Metabolically Competent Human Hepatoma Cell Line Hep-G2: Results with 15 Naturally Occuring Substances," Anticancer Research 21:461-470 (2001).
Liebers et al., "Overview on denominated allergens," Clinical and Experimental Allergy 26:494-516 (1996).
Taylor et al., " The Role of Glycosylation in Flavonol-Induced Pollen Germination," Adv. Exp. Med. Biol 439:35-44 (1998).
Meltz et al., "Activity of the Plant Flavanol Quercetin in the Mouse Lymphoma L5178Y TK +/− MUTATION, DNA Single-Strand Break, and Balb/c 3T3 Chemical Transformation Assays," Mutation Research, 88:317-324 (1981).
Nagao et al., "Mutagenicities of 61 Flavonoids and 11 Related Compounds," Environmental Mutagenesis 3:401-419 (1981).
Snyder et al., "Evaluation of the Clastogenic, DNA Intercalative, and Topoisomerase II-Interactive Properties of Bioflavonoids in Chinese Hamster V79 Cells," Environmental and Molecular Mutagenesis 40:266-276 (2002).
Kuhn, et al., "Über das Flavonol-glykosid aus Crocus-Pollen" Chem. Ber. 77:196-202 (1944).
Bonaccorsi et al., Flavonol Glucoside Profile of Southern Italian Red Onion (Allium cepa L.), J. Agric. Food Chem. 53:2733-2740 (2005).
Czeczot et al., "Isolation and studies of the mutagenic activity in the Ames test of flavonoids naturally occurring in medical herbs" Mutation Research, 240:209-216 (1990).
MacGregor et al., "Mutagenicity of Plant Flavonoids: Structural Requirements for Mutagenic Activity in *Samonella typhimurium*" Mutation Research 54:297-309 (1978).
Mullen et all., "HPLC-MS2 Metabolite Profiling of Quercertin Methyl, Glucuronyl, Glucosyl and Sulpho-Conjugates in Plasma and Urine After the Ingestion of Onions by Human Volunteers" Journal of Oil Palm Research, pp. 65-80 (Special Issue—Apr. 2006).

* cited by examiner

REDUCTION OF IN VITRO GENOTOXICITY OF POLLEN EXTRACTS BY REMOVAL OF FLAVONOIDS

CROSS REFERENCE TO RELATED APPLICATIONS

This application is a U.S. nationalization under 35 U.S.C. §371 of International Application No. PCT/EP2010/057935, filed Jun. 7, 2010, which claims priority to European patent application nos. EP09305517.6, filed Jun. 5, 2009, and EP09174479.7, filed Oct. 29, 2009. The disclosures set forth in the referenced applications are incorporated herein by reference in their entireties.

The invention relates to grass pollen extracts containing reduced amount of flavonoid glycosides in order to minimize the risks of genotoxicity of the grass pollen extracts. The invention also relates to a method of preparing grass pollen extracts containing reduced amount of flavonoid glycosides by ultrafiltration. Flavonoid glycosides are naturally present in grass pollen extracts and they have been identified as being the sources of flavonoid aglycones, which are genotoxic in vitro, under the influence of enzymes contained in the grass pollen extracts.

According to ICH guideline S2B of Jul. 16, 1997, registration of pharmaceuticals requires a comprehensive assessment of their genotoxic potential. The standard test battery recommended includes an in vitro test with cytogenetic evaluation of chromosomal damage with mammalian cells or an in vitro mouse lymphoma thymidine kinase gene mutation assay (MLA/TK).

As per the ICH-S2B guidelines, the in vitro MLA/TK test was performed on pollen extracts and/or raw materials from five grass species intended to be used for desensitization of patients allergic to grass pollens.

It was found that the freeze-dried extract of pollens exhibited no genotoxic potential in vitro in a MLA/TK test when using a 3-hour short term treatment with or without metabolic activation. Nevertheless, positive results were observed in the MLA/TK test under a very specific condition, namely when the test was performed using a continuous 24-h treatment without metabolic activation ("S9-"). The genotoxic potential observed in this specific condition slightly decreased during the manufacturing process of freeze-dried pollen extracts. Therefore, the in vitro genotoxic activity was not introduced during this process but originated from the pollen raw materials. In fact, it was found to be associated with pollens from the 5 grass species used to manufacture the extracts, whatever the grass pollen supplier.

Although the freeze-dried pollen extracts exhibited no genotoxicity in vivo in two different assays, to preclude any putative risk, the causative agent for the in vitro genotoxicity was sought.

As the observed in vitro genotoxicity was linked to all species of grass pollen used to manufacture the extracts, whatever the grass pollen supplier, it was most likely due to intrinsic substance(s) of grass pollens rather than to external genotoxic contaminants from the agroenvironment. Indeed, it is virtually impossible to envision the same pollutant contaminating multiple grass pollen species originating from several suppliers. However, one cannot totally exclude that external genotoxic contaminants might explain the genotoxic potential, at least partly and in some cases.

Thus, the inventors proceeded with quantifying external genotoxic contaminants in grass pollen raw materials. It was found that the following environmental genotoxic contaminants were undetectable and/or below the calculated limit doses in grass pollen raw materials: artificial radioelements ($^{134}$Cs and $^{137}$Cs), heavy metals (Cd, Ni, Cr), mycotoxins (aflatoxins B1&B2, G1&G2; deoxynivalenol [DON]/vomitoxin; fumonisins B1&B2; ochratoxin A; zearalenone), the polycyclic aromatic hydrocarbon benzo[a]pyrene.

The inventors then set up a study to determine which intrinsic substance(s) of the grass pollens was(were) responsible for the observed genotoxic profile of the grass pollen raw materials and extracts. Grass pollens were assessed for the presence of caffeic and chlorogenic acids, coumarin, alkaloids, and flavonoids.

Among those, only flavonoids were detected in the grass pollens, in the form of flavonoid glycosides. The latter are not known to be genotoxic in vitro but flavonoid aglycones are.

It was therefore hypothesised that the in vitro genotoxic potential observed with grass pollens is due to deglycosylation by specific enzymes of non-genotoxic flavonoid glycosides into flavonoid aglycones, both the flavonoid glycosides and the enzymes being extractable from the grass pollens.

It was indeed demonstrated that flavonoid glycosides are identified within grass pollens in the form of: isorhamnetin-diglucoside, quercetin-diglucoside and kaempferol-diglucoside. Under the conditions of the 24-h long term protocol of the MLA/TK test, those flavonoid glycosides are deglycosylated into their flavonoid aglycone counterparts (i.e. isorhamnetin, quercetin and kaempferol, respectively), provided they are in the presence of the grass pollen proteins. In particular, ~20% of quercetin-diglucoside are deglycosylated into quercetin, the latter being by far the most genotoxic of the three flavonoid aglycones released from grass pollens.

Flavonoids have been previously reported to be tightly adsorbed to protein by physical and chemical interactions within tree, grass, herbaceous and flowering plant pollen extracts.

For instance, the U.S. Pat. No. 5,770,698 described removal of non-allergenic undesirable compounds from aqueous pollen extracts by means of disrupting electrostatic forces, hydrophobic or other physical forces, in particular by using acid or alkaline materials, salts and electric currents (electrophoresis). Removal of flavonoids and/or glycosides was more specifically contemplated as these compounds were described as likely to modulate the normal biological response of mast cells, basophils, polymorphonuclear leucocytes and neutrophils. In particular, the flavonoids which are firmly adsorbed to proteins were described to resist simple dialysis or ultrafiltration at neutral pH through membrane of 10 kDa nominal cut-off. U.S. Pat. No. 5,770,698 more specifically describes removal of pigments, including flavonoids, by dialysis of a pollen extract in water acidified to pH 2 against 100 volumes of water (pH 6-7.5). This method is described to remove 15-65% w:w of adsorbed pigments relative to dry weight of the original pollen protein preparation. However, U.S. Pat. No. 5,770,698 also points out at possible drawbacks associated with this method, i.e. denaturation or loss of essential structural protein determinants due to exposure of proteins to such a low pH.

Removal of pigments, including flavonoids, physically adsorbed to ragweed pollen allergens was also described to be performed by acidification of the aqueous pollen extract to pH 2 and further subjecting the extract to dialysis against acidified water pH 2 (Hidvégi T, Berrens L, Varga L, Marañon F, Schmidt B, Kirschfink M, Füst G. Clin Exp Immunol. 1997 April; 108(1):122-7). This method is described to remove 37% w/w of adsorbed (flavonoid) pigment material.

However, it was unexpectedly found that flavonoids can be successfully removed from aqueous pollen extracts simply by increasing the extent of ultrafiltration, without adversely affecting the immunogenicity of the allergens. Indeed, ultrafiltration can be detrimental to proteins as they are submitted to high shearing forces in the course of the process. Therefore, intensifying ultrafiltration of an aqueous pollen extract could have caused alteration of the allergens. Furthermore, since flavonoids and flavonoid glycosides are known to be firmly adsorbed to proteins, it was unpredictable that a method based merely on ultrafiltration with water would achieve disrupting the interaction flavonoids/flavonoid glycosides and proteins.

The optimized ultrafiltration method described herein made it possible to prepare grass pollen extract containing less than 0.001% (w/w) of each of isorhamnetin, quercetin and kaempferol (as expressed in aglycone equivalents) in freeze-dried extracts of grass pollens (i.e. less than 0.001 g of each of isorhamnetin, quercetin and kaempferol—as expressed in aglycones—per 100 g of freeze-dried extracts of grass pollens). For comparison, the freeze-dried grass pollen extract previously obtained using the non-optimized ultrafiltration method contained total 0.17% (w/w) of flavonoids (as expressed in aglycone equivalents) (mean value on three batches).

A concentration of 0.001% (w/w) of flavonoid aglycone in freeze-dried extract of grass pollens is equivalent to weight ratio 0.0057-0.0064 g of flavonoid aglycone in 100 g of pollen starting material, as 1 g of lyophilisate is obtained starting from 5.7-6.4 g of pollen raw material.

As a consequence, the amount of flavonoids administered with a 300-IR tablet/day made of grass pollen extracts obtained using the optimized ultrafiltration step would lead to a theoretical daily intake below 0.15 µg of pollen-derived flavonoids (as expressed in flavonol diglucoside). For comparison, the daily intake of flavonoids through common diet (fruits, vegetables) is of 20 mg to 1 g (Middleton E Jr, Kandaswami C, Theoharides T C. Pharmacol. Rev. 2000; 52: 673-751).

The putative risk associated with those very low amounts of flavonoids is thus totally abolished by the optimized ultrafiltration step, leading to a virtually complete removal of flavonoids from the grass pollen extracts, below the detection limits of highly-sensitive analytical methods such as HPLC-DAD.

DEFINITIONS

As used herein, an "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996). An allergen may be any amino acid chain likely to trigger an allergic response, including short peptides of about 6 to 20 aminoacids, polypeptides, or full proteins. They can be glycosylated.

Non limitative examples of allergens include pollen allergens (such as tree, herb, weed, and grass pollen allergens), insect allergens (such as saliva and venom allergens, e.g., cockroach and midges allergens, hymenopthera venom allergens), mite allergens, animal allergens (from e.g. dog, cat, horse, rat, mouse etc.), and food allergens.

Important pollen allergens are such allergen of the genus *Ambrosia*; allergen of the genus *Lolium*; allergen of the genus *Cryptomeria*; allergen of the genus *Alternaria*; allergen of the genus *Alder*; allergen of the genus *Betula*; allergen of the genus *Quercus*; allergen of the genus *Olea*; allergen of the genus *Artemisia*; allergen of the genus *Plantago*; allergen of the genus *Parietaria*; allergen of the genus *Cupressus*; allergen of the genus *Thuya*; allergen of the genus *Chamaecyparis*; allergen of the genus *Periplaneta*; allergen of the genus *Agropyron*; allergen of the genus *Secale*; allergen of the genus *Triticum*; allergen of the genus *Cynorhodon*; allergen of the genus *Juniperus*; allergen of the genus *Dactylis*; allergen of the genus *Festuca*; allergen of the genus *Poa*; allergen of the genus *Avena*; allergen of the genus *Holcus*; allergen of the genus *Anthoxanthum*; allergen of the genus *Arrhenatherum*; allergen of the genus *Agrostis*; allergen of the genus *Phleum*; allergen of the genus *Phalaris*; allergen of the genus *Paspalum*; and allergen of the genus *Sorghum*.

Examples of various known pollen allergens derived from some of the above-identified genus include: *Cynorhodon* Cyn d 1; *Ambrosia* (artemisiifolia) Amb a 1; Amb a 2; Amb a 3; Amb a 4; *Lolium* (perenne) Lol p 1; Lol p 2; Lol p 3; Lol p 4; Lol p 5; Lol p 9; *Cryptomeria* (japonica) Cry j 1; Cry j 2; Cry j 3; *Juniperus* (sabinoides ou virginiana) Jun s 1; Jun v 1; *Juniperus* (ashei) Jun a 1; Jun a 2; *Dactylis* (glomerate) Dac g 1; Dac g 5; *Poa* (pratensis) Poa p 1; Poa p 5; *Phleum* (pratense) Phl p 1; Phl p 5; *Anthoxanthum* (odoratum) Ant o 1; Ant o 5; *Betula* (verrucosa) Bet v 1; Bet v 2; Bet v 4 and *Sorghum* (halepensis) Sor h 1.

Insect allergens, mite allergens, animal allergens may include in particular allergens of the genus of *Blomia*; allergens of the genus *Dermatophagoides*; allergens of the genus *Blattella*; and allergens of the genus *Apis*; allergens of the genus *Felis*; allergens of the genus *Canis*. Preferred allergens include: *Blomia tropicalis* Blo t 1; Blo t 3; Blo t 5; Blo t 12; *Dermatophagoides* (pteronyssinus or farinae) Der p 1; Der p 2; Der p 3; Der p 5; Der p 7; Der f 1; Der f 2; Der f 3; Der f 5; Der f 7; *Felis* (domesticus) Fel d 1; *Canis* (familiaris) Can f 1; Can f 2; *Blattella* (germanica) Bla g 1; Bla g 2.

In the context of the invention, the terms "to treat", "treating" or "treatment" means reversing, alleviating, or inhibiting the course of a pathological reaction of the immune system or one or more symptoms thereof.

In the context of the invention, the terms "to prevent" or "preventing", means the onset of a pathological reaction of the immune system or one or more symptoms thereof.

As used herein, the term "patient" preferably denotes a human, but may more generally a mammal, such as a rodent, a feline, a canine, and a primate.

Method of Reducing In Vitro Genotoxicity of Pollen Extracts

Pollen raw materials, and pollen extracts (conventionally prepared by extracting allergens from pollen with aqueous solution, followed by separation, clarification by filtration, and ultrafiltration on a 1-kDa membrane with washing with 2.5 volumes of purified water) were found to be genotoxic in vitro in a MLA/TK test when using a continuous 24-h treatment without metabolic activation ("S9-").

Flavonoids were identified by the inventors as the agents responsible for this genotoxic activity in vitro.

The invention thus relates to a method of reducing in vitro genotoxicity of a pollen extract which comprises the step consisting of reducing the amount of a flavonoid in the pollen extract.

According to the invention the flavonoid may be at least one flavonoid aglycone or at least one flavonoid glycoside, preferably at least one flavonoid glycoside. The flavonoid glycoside may be in particular a glycosylated form of flavone, rhamnetin, isorhamnetin, kaempferol, or quercetin. Preferably the flavonoid is selected from the group consisting of isorhamnetin-diglucoside, quercetin-diglucoside, kaempferol-diglucoside, isorhamnetin-glucoside, quercetin-glucoside, kaempferol-glucoside, isorhamnetin-malonuyl-glucoside, quercetin-malonuyl-glucoside, and kaempferol-malonuyl-glucoside.

Isorhamnetin-glucoside, quercetin-glucoside, kaempferol-glucoside, isorhamnetin-malonuyl-glucoside, quercetin-malonuyl-glucoside, and kaempferol-malonuyl-glucoside have been identified by the inventors as flavonoids present in ragweed pollen.

Still preferably, the method of reducing in vitro genotoxicity according to the invention comprises reducing the amount of isorhamnetin-diglucoside, quercetin-diglucoside and kaempferol-diglucoside in the pollen extract.

Also preferably, the method of reducing in vitro genotoxicity according to the invention comprises reducing the amount of isorhamnetin-glucoside, quercetin-glucoside, kaempferol-glucoside, isorhamnetin-malonuyl-glucoside, quercetin-malonuyl-glucoside, and kaempferol-malonuyl-glucoside.

As used herein, "reducing the amount of a flavonoid in the pollen extract" is meant for a detectable reduction of the quantity of at least one flavonoid in the pollen extract, e.g. by at least 2-fold, preferably 10-fold, 20-fold, 50-fold, 100-fold, 200-fold or 300-fold. Preferably, flavonoids are completely removed from the pollen extract, i.e. they are removed to an extent such that their quantity or concentration is below the detection limits.

According to a preferred embodiment of the method of the invention, the amount of each flavonoid in the pollen extract is below 0.002%, preferably 0.001%, expressed in weight of flavonoid on the weight of pollen derived fraction (i.e. 0.002 g, preferably 0.001 g, of flavonoid per 100 g of pollen derived fraction), the amount of flavonoid being expressed in aglycone equivalent.

The pollen derived fraction is the fraction of material deriving from the pollen, thus excluding any additive used in the course of the purification process, such a salts, freeze-drying additives, etc.

The "pollen extract" may be a tree pollen extract, a grass pollen extract, a herb pollen extract, a weed pollen extract, or mixtures of thereof. For instance the pollen extract may be a mixture of tree pollen extracts, a mixture of grass pollen extracts, a mixture of herb pollen extracts, a mixture of weed pollen extracts, or a mixture of weed pollens, or a mixture of tree and/or grass and/or herb and/or weed pollen extracts. The pollen may be a mixture of tree pollens, or a mixture of grass pollens, or a mixture of herb pollens, or a mixture of weed pollens, or a mixture of tree and/or grass and/or herb and/or weed pollens. The pollen extract may then be an extract of these pollen mixtures. A pollen extract contains pollen allergens.

Preferably, the pollen extract is an extract of a mixture consisting of, or comprising, cocksfoot, meadow-grass, rye-grass, sweet vernal-grass and timothy grass pollens.

The method of reducing in vitro genotoxicity according to the invention may be implemented by using any method available to the one skilled in the art to reduce the amount of flavonoids in a pollen extract.

Methods such as described in U.S. Pat. No. 5,770,698 or as published by Hidvègi et al. (Clin Exp Immunol. 1997 April; 108(1):122-7), which involve acidifying an aqueous pollen extracts to a pH below 3, preferably to about pH 2, followed by dialysis, may be used. However, due to these drastic conditions, the allergens may undergo denaturation. It is thus preferred to use alternative methods to reduce flavonoid content of pollen extracts.

Preferably removal of flavonoids is performed by ultrafiltration of pollen extract(s) with water, preferably containing ammonium bicarbonate.

Indeed, the inventors demonstrated that contrary to prior assumptions, ultrafiltration with purified water, i.e. ultrafiltration at neutral pH, can successfully be used to reduce the amount of, or remove, flavonoids. To that end, the extent of purification of the pollen extract by ultrafiltration was increased. However, as increasing the extent of ultrafiltration could lead to allergen degradation, an optimized ultrafiltration method was designed which can be used to implement the method of reducing in vitro genotoxicity according to the invention. A more detailed description of this optimized ultrafiltration method is given below. All the features disclosed in connection with this optimized ultrafiltration method must be considered as disclosed in combination with the instant method of reducing in vitro genotoxicity of pollen extract.

Purified Pollen Extracts with Reduced In Vitro Genotoxicity

The above method of reducing in vitro genotoxicity of a pollen extract, especially when implemented using an optimized ultrafiltration method according to the invention, advantageously leads to pollen extracts having a amount of each flavonoid below 0.002%, expressed in weight of flavonoid on the weight of pollen derived fraction (i.e. below 0.002 g of flavonoid per 100 g of pollen derived fraction), the amount of flavonoid being expressed in flavonoid equivalents.

Accordingly, the invention also provides a purified pollen extract wherein each flavonoid is contained in amount which is less than 0.002 g per 100 g of pollen derived fraction, as expressed in aglycone equivalent Preferably each flavonoid is contained in amount which is less than 0.001 g per 100 g of pollen derived fraction, as expressed in aglycone equivalent.

The pollen extract may be such as defined above. Preferably, the pollen extract is an extract of a mixture consisting of, or comprising, cocksfoot, meadow-grass, rye-grass, sweet vernal-grass and timothy grass pollens.

The purified pollen extract is essentially devoid of flavonoids and, as a consequence, does no longer exhibit in vitro genotoxicity in the MLA/TK test.

Accordingly, the purified pollen extract according to the invention may be formulated in the form of a pharmaceutical composition, together with a pharmaceutically acceptable carrier. Such purified pollen extract, optionally provided in the form of a pharmaceutical composition, may advantageously be used for treating and/or preventing pollen allergy, by desensitisation, while minimising the risk of induced genotoxicity in the patient receiving the treatment.

The invention thus further relates to a purified pollen extract wherein each flavonoid is contained in amount which is less than 0.002 g, preferably less than 0.001 g, per 100 g of pollen derived fraction, as expressed in aglycone equivalent, for use for treating and/or preventing a pollen allergy, in particular for pollen allergy desensitisation. This pollen allergy treatment or prevention is associated with reduced risk of genotoxicity.

The invention also relates to a method of treating and/or preventing a pollen allergy, in particular a method of pollen allergy desensitisation, which method comprises repeatedly administering a patient in need thereof with a purified pollen extract wherein each flavonoid is contained in amount which is less than 0.002 g preferably less than 0.001 g, per 100 g of pollen derived fraction, as expressed in aglycone equivalents.

Administration of the pollen extract or pharmaceutical composition may be maintained for instance for a period of less than 6 weeks to more than 3 years.

The pollen allergy may be a tree pollen allergy, a grass pollen allergy, a herb pollen allergy, a weed pollen allergy, or combined allergies. However, preferably a tree pollen extract is used to treat a tree pollen allergy, a grass pollen extract is used to treat a grass pollen allergy, a weed pollen extract is used to treat a weed pollen allergy, and an herb pollen extract is used to treat an herb pollen allergy.

Optimized Method of Ultrafiltration

Purified allergen extracts, in particular purified pollen extracts and mite extracts, have been previously prepared by extracting the allergens from pollen or house dust mite raw material with an aqueous solution, followed by separation, clarification by filtration, concentration and ultrafiltration on a 1-kDa membrane with washing with 2.5 volumes of purified water.

The inventors succeeded in developing an optimized ultrafiltration method which enables for increasing the extent allergen purification without detrimental effect on the quality of the allergen preparation, e.g. protein denaturation. More specifically, analysis of allergen extracts by each of IEF (isoelectric focusing), SDS-PAGE electrophoresis and immunoblots show that the profile of the allergen extracts are unaltered by the modification of the ultrafiltration method. Altogether the protein content and immunological activity of the purified allergen are unchanged.

However, when the allergen is a pollen allergen, the optimized ultrafiltration method enables to remove flavonoid below detectable limits.

The same method was applied to purify mite allergens, in particular house dust mite allergens, and enabled to increase the level of purity of the allergen preparation.

Accordingly, the optimized ultrafiltration method should find general application in the purification of any allergen extracts, i.e. pollen (tree-, grass-, herb-, weed-), insect, venom allergens, mite, animal, and food allergens, venom allergens.

The method of preparing purified allergen extract according to the invention may comprise a step of ultrafiltration of an aqueous allergen extract on a 1-10 kDa membrane with at least 5 volumes of purified water.

As compared with ultrafiltration on a 1-kDa membrane with washing with 2.5 volumes of purified water, these conditions enable to remove essentially all flavonoids present in a pollen extract. However, when the purified pollen extract is then submitted to final filtration on a 0.22-µm filter, to sterilise the extract, filtration clogging is observed. The same phenomenon was observed with mite extract. Without willing to be bound to a theory, it is thought that the increased volumes of water used for ultrafiltration lead to a decreased ionic strength which may in turn induce this filtration clogging.

This drawback was eliminated by using an ammonium bicarbonate solution for ultrafiltration instead of purified water. Other buffered aqueous solutions, such as in particular phosphate buffered solutions, may be used instead of the ammonium bicarbonate solution. Alternatively, ammonium bicarbonate or phosphate buffer salt may be added to the purified allergen extract after ultrafiltration, but before an optional subsequent sterilisation filtration.

Accordingly, the invention relates to a method of preparing purified allergen extract, which method comprises a step of ultrafiltration of an aqueous allergen extract on a 1-10 kDa membrane with at least 5 volumes of an aqueous solution selected from the group consisting of purified water and a buffered solution, such as an ammonium bicarbonate solution and a phosphate buffered solution. In particular, said ultrafiltration may be performed on a 2-10 kDa, preferably 5-10 kDa membrane, with at least 10 volumes of said aqueous solution. According to an embodiment, at most 30 volumes of aqueous solution may be used.

The number of volumes of aqueous solution used for ultrafiltration is expressed by reference to the volume of aqueous allergen extract loaded on the membrane.

Preferably in the method of the invention, the ultrafiltration step is performed with a 2-10 kDa membrane, preferably a 5-10 kDa membrane, still preferably with a 5 kDa membrane.

Where the aqueous solution is purified water, it is preferred that between 5 and 15 volumes of purified water, still preferably 10, 11, 12, 13, 14 or 15 volumes of purified water, be used for ultrafiltration, as a decrease in allergenicity could be observed with higher volumes of purified water.

Where the aqueous solution is ammonium bicarbonate solution or another buffered solution such as phosphate buffered solution, up to 30 volumes of solution may be used without detrimental effect on the allergenicity of the preparation. Higher volumes could be used, but without significant gain in term of extent of purification. Therefore, it is preferred that 10 to 30 volumes, preferably 10 to 20, still preferably 10 to 15 volumes, most preferably 11, 12, 13, 14 or 15 volumes of ammonium bicarbonate solution be used for ultrafiltration.

The ammonium bicarbonate solution may contain between about 100 to 150 ppm of ammoniac, preferably about 120 ppm of ammoniac. Such ammoniac contents may be achieved with ammonium bicarbonate solutions with concentration ranging from 0.4 to 0.8 g/L, preferably 0.46 g/L to 0.7 g/L, still preferably 0.5 to 0.6 g/L, most preferably 0.56 g/L.

The method of preparing purified allergen extract may thus comprise a step of ultrafiltration of an aqueous allergen extract on a 5-10 kDa membrane with 10 to 30 volumes of a 0.4 g/L to 0.8 g/L ammonium bicarbonate solution.

Preferably, ultrafiltration of the aqueous allergen extract is performed on a 5 kDa membrane with 10 to 20 volumes, still preferably 10 to 15 volumes, most preferably 11, 12, 13, 14 or 15 volumes, of a 0.5 to 0.6 g/L ammonium bicarbonate solution.

Most preferably, ultrafiltration of said aqueous allergen extract is performed on a 5 kDa membrane with 15 volumes of a 0.56 g/L ammonium bicarbonate solution.

The allergen extract is preferably a mixture of pollen extracts consisting of, or comprising, cocksfoot, meadow grass, rye-grass, sweet vernal-grass and timothy grass extracts.

The optimized ultrafiltration process enables for preparing purified pollen extract containing a total amount of flavonoids below 0.001%, expressed in weight of dried flavonoids on the weight of dried pollen extract (i.e. 0.001 g of dried flavonoids per 100 g of dried pollen extract). By comparison, the purified pollen extract prepared using the previous ultrafiltration process previously used (1 kDa membrane with washing with 2.5 volumes of purified water) contain 0.36% (w/w) of flavonoids.

Another preferred allergen extracts is a house dust mite extract, in particular an allergen extract from *Blomia tropicalis*, or *Dermatophagoides pteronyssinus* or *Dermatophagoides farinae*. Preferably the allergen extracts comprises Der p I and/or Der p II.

The method of preparing purified allergen extract according to the invention may further comprise a step of filtration on a 0.22 μm filter.

The method of preparing purified allergen extract according to the invention may comprise drying, e.g. by freeze-drying or spray-drying, of the purified allergen extract, for subsequent storing or formulation into a solid pharmaceutical composition, such as a tablet.

The method of preparing purified allergen extract according to the invention may also further comprise a step of formulating said purified pollen extract into a pharmaceutical composition.

The invention further provides a purified allergen extract which is obtainable by the method of preparing purified allergen extract according to the invention.

The invention also relates to a pharmaceutical composition comprising a purified allergen extract, which pharmaceutical composition is obtainable by the method of preparing purified allergen extract and formulating said purified pollen extract into a pharmaceutical composition.

Preferably, the pharmaceutical composition is a tablet for use for sublingual allergy desensitisation.

Pharmaceutical Compositions

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art.

In the frame of the invention, the pharmaceutical compositions can include any conventional vaccination adjuvant, including heat-labile enterotoxin (LT), cholera-toxin (CT), cholera toxin B subunit (CTB), polymerised liposomes, mutant toxins.

For oromucosal administration, the adjuvants may preferably be a *Bifidobacterium*, a lactic acid bacterium (either in the form of a cell suspension, freeze-dried cells, a lysate, purified sub-components, or purified molecules), or a combination of a corticosteroid with vitamin D3 or any metabolite or analog of the latter.

Advantageously, where mucosal administration is contemplated, the adjuvant may be a synthetic particulate vector that comprises a non-liquid hydrophilic core which comprises a cross-linked polysaccharide. Such a formulation was found to be particularly efficient in inducing immune tolerance. The particles which can be used are described in the international patent application PCT/IB2007/002379.

Briefly, the cross-linked polysaccharide may be derived from any saccharide monomers, preferably glucose. The polysaccharides preferably have a molecular weight between 2,000 to 100,000 daltons, and most preferably 3,000 to 10,000 daltons. Preferred polysaccharides are starch (glucose alpha 1-4 polymers) and dextran (glucose alpha 1-6 polymers derived from bacteria), or hydrolysates thereof such as dextrins or maltodextrins.

Ionic groups, i.e. anionic (e.g. sulfate or carboxylate) or cationic groups (e.g. quaternary ammonium ions, and primary, secondary, or tertiary amines) are optionally grafted to the core of cross-linked polysaccharide (preferably 0 to 3 milliequivalents, more preferably 0 to 2 milliequivalents, of ionic charge per gram).

Optionally, the cross-linked polysaccharide core is at least partially coated with a layer of amphiphilic compounds and/or a layer of lipidic compounds.

The diameter of the particle may be comprised between 10 nm and 5 μm and preferably between 20 and 200 nm.

For parenteral administration in an aqueous solution, for example, the solution should be suitably buffered if necessary and the liquid diluent first rendered isotonic with sufficient saline or glucose. These particular aqueous solutions are especially suitable for intramuscular and subcutaneous administration. In this connection, sterile aqueous media which can be employed will be known to those of skill in the art in light of the present disclosure.

Preferably, the pharmaceutical composition is to be administered by the mucosal route, more preferably by the oromucosal route, and most preferably by the sublingual route. As such the pharmaceutical composition and the medicament are preferably formulated in a way adapted for such administration routes.

Mucosal administration denotes any administration method, wherein the formulation in part or in full comes into contact with a mucosa. Mucosa refers to the epithelial tissue that lines the internal cavities of the body. The mucosal surface may be selected from the group consisting of a nasal, buccal, oral, vaginal, ocular, auditory, pulmonary tract, urethral, digestive tract, and rectal surface.

Oromucosal administration comprises any administration method, wherein the formulation in part or in full comes into contact with the mucosa of the oral cavity and/or the pharynx of the patient. It includes in particular sublingual, perlingual (i.e. through the tongue mucosa) and oral administrations.

Preferably, the pharmaceutical composition is formulated in the form of a tablet for sublingual administration.

According to an embodiment the pharmaceutical composition comprises an extract of a mixture of pollens consisting of, or comprising, cocksfoot, meadow-grass, rye-grass, sweet vernal-grass and timothy grass pollens.

According to another embodiment the pharmaceutical composition comprises a house dust mite allergen, such as an allergen of *Blomia tropicalis* or of *Dermatophagoides pteronyssinus* or *Dermatophagoides farinae*. Preferably the allergen is Der p 1 and/or Der 2 and/or Der f 1 and/or Der f 2.

The invention will be further illustrated in view of the following figures and examples.

FIGURES

FIG. 1 shows cumulated area of the peaks corresponding to the different flavonoids found in a grass pollen extracts before (0 h) and after a 3-h and a 24-h incubation at 37° C.

Figure 2:
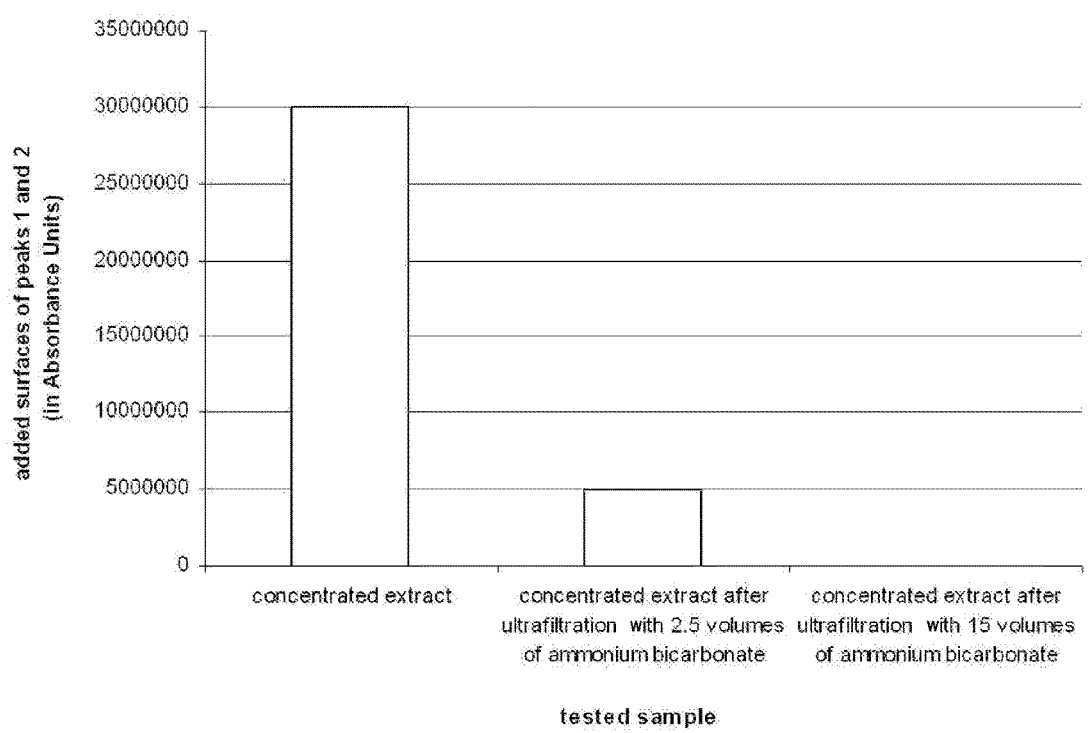

FIG. 2 illustrates the amount of flavonoids contained in a concentrated extract of 5 grass pollens before and after ultrafiltration with 2.5 volumes (as per the previous non-optimized manufacturing process) and 15 volumes (as per the optimized manufacturing process) of 120 ppm ammonium bicarbonate. Results are expressed as the sum of the integrated surfaces of peak 1 (RT 14.83 min) and peak 2 (RT 15.00 min).

EXAMPLES

Example 1

Raw Materials and Initial Process (i.e. Non Modified Process) of Preparing Pollen Extract Raw materials consisted of defatted pollen of cocksfoot, meadow grass, rye-grass, sweet vernal-grass and timothy grass.

The process of purification used to prepare purified pollen extract, or purified mixture of pollen extracts typically comprise the steps of:

optionally mixing pollens originating from different species, if a mixture of pollens is intended to be purified;

extracting the pollens by contacting the pollens with extraction solution, typically an aqueous solution such as distilled water or a buffered distilled water solution;

separating the aqueous phase from the solid phase, for instance by centrifugation, to recover the aqueous phase which contains the allergens extracted from the pollen (pollen extract);

clarifying by filtration the pollen extract;

concentrating the pollen extract by passage on a 1-kDa or 5-kDa membrane;

submitting the retentate to ultrafiltration on a 1-kDa membrane with washing with 2.5 volumes of purified water; and filtrating through a 0.22-μm filter to sterilise the purified pollen extract.

The purified pollen extract is then typically freeze-dried and formulated into an appropriate pharmaceutical composition, e.g. a tablet.

Pollen raw materials and pollen extracts prepared according to the above process have been found to be genotoxic in a Mouse Lymphoma Assay (MLA)/TK test when using a continuous 24-h treatment without metabolic activation ("S9-").

Example 2

Quantification of External Genotoxic Contaminants

Four groups of genotoxic elements from the agroenvironment have been assessed in grass pollen raw materials, as summarized below in table 1:

TABLE 1

| Genotoxic contaminants tested in raw materials tablets | | | | |
|---|---|---|---|---|
| Class of potential contaminants | Quantification method | Samples tested | Results | Outcomes |
| Artificial radioelements $^{134}$Cs and $^{137}$Cs | Gamma spectrometry | 2 batches (from 2 different suppliers) for either cocksfoot, meadow grass, rye-grass, sweet vernal-grass or timothy pollen species = a total of 10 batches | No activity due to the artificial radioelements $^{134}$Cs and $^{137}$Cs was detected in grass pollen raw materials | Complies with the EEC regulation (Council Regulation (EC) No 616/2000 of 20 March 2000) |
| Heavy metals (Cd, Ni and Cr) | Cadmium (Cd): Inductively Coupled Plasma-Mass Spectrometry (ICP-MS) after mineralization | a total of 17 batches of cocksfoot, meadow grass, rye-grass, sweet vernal-grass or timothy pollen species from 3 suppliers | Cd is undetectable (<0.5 ppm) in all tested batches | Cd is largely below (at least 250 fold) the calculated limit dose (125 ppm) |
| | Nickel (Ni) and chromium (Cr): Graphite Furnace Atomic Absorption Spectrometry (GFAAS) | 2 batches (from 2 different suppliers) for either cocksfoot, meadow grass, rye-grass, sweet vernal-grass or timothy pollen species = a total of 10 batches | Ni and Cr were <10 ppm and <2 ppm, respectively, in the tested batches | Ni and Cr are largely below (more than 10 fold and 60 fold, respectively) the calculated limit dose (125 ppm) |
| Mycotoxins (aflatoxins B1&2 G1&2; DON*/ vomitoxin; fumonisins B1&2; ochratoxin A; zearalenone) | HPLC | 2 batches (from 2 suppliers, except for 1 species) for either cocksfoot, meadow grass, rye-grass, sweet vernal-grass or timothy pollen species = a total of 10 batches | undetectable or just above the detection limit (aflatoxin B1 in 1 batch) in all tested batches | all mycotoxins are largely below (1,250 fold or more) the calculated limit doses (depending on the considered alfatoxin) |
| Benzo[a]pyrene | isotope dilution Gas Chromatography followed by Mass Spectrometry (GC-MS) | 2 batches (from 2 different suppliers) for either cocksfoot, meadow grass, rye-grass, sweet vernal-grass or timothy pollen species = a total of 10 batches | undetectable or just above the detection limit (in 1 batch) in all tested batches | benzo[a]-pyrene is largely below (at least 1.6 10$^5$ fold) the calculated limit dose (125 ppm) |

*Deoxynivalenol.

All four categories of contaminants which could lead to a genotoxic potential in vitro were undetectable and/or largely below the calculated limit doses according to the appropriate (i.e. health of food) guidelines, in at least 10 batches of raw materials used to make grass pollen tablets.

Thus, the genotoxic profile of grass pollen raw materials and extracts must be explained by grass pollen intrinsic substance(s) only.

Example 3

Search for Intrinsic Substances with a Genotoxic Potential In Vitro

Four substances or substance groups which might be grass pollen intrinsic substances explaining the observed in vitro genotoxic potential were selected for further analysis:
  chlorogenic and caffeic acids (Fung V A, Cameron T P, Hughes T J, Kirby P E, Dunkel V C. Mutat. Res. 1988; 204: 219-228.),
  coumarin (Kevekordes S, Spielberger J, Burghaus C M, Birkenkamp P, Zietz B, Paufler P, Diez M, Bolten C, Dunkelberg H. Anticancer Res. 2001; 21: 461-469; Möller M, Stopper H, Haring M, Schleger Y, Epe B, Adam W, Saha-Moller C R. Biochem. Biophys. Res. Commun. 1995; 216: 693-701),
  alkaloids (Liu S X, Cao J, Yuan J, Huang P, Shua P Q, Honma M. Zhongguo Zhong Yao Za Zhi. 2003; 28: 957-961), and
  flavonoids (Caria H, Chaveca T, Laires A, Rueff J. Mutat. Res. 1995; 343: 85-94; Müller L and Kasper P. Mutat. Res. 2000; 464: 19-34 (review); Antognoni F, Ovidi E, Taddei A R, Gambellini G, Speranza A. Ahern. Lab. Anim. 2004; 32: 79-90; Meltz M L, McGregor J T. Mutat. Res. 1981; 88: 317-324; Snyder R D, Gillies P J. Environ. Mol. Mutagen. 2002; 40: 266-276; Nagao M, Morita N, Yahagi T, Shimizu M, Kuroyanagi M, Fukuoka M, Yoshihira K, Natori S, Fujino T, Sugimura T. Environ. Mutagen. 1981; 3: 401-419).

Importantly, two forms of flavonoids can be distinguished:
  flavonoid glycosides as exemplified by hyperoside:

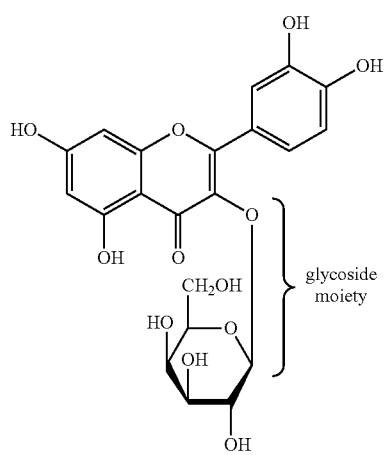

and flavonoid aglycones, as exemplified by quercetin (the aglycone of hyperoside)

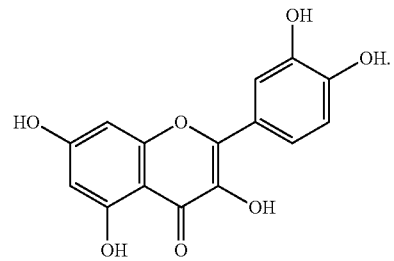 [SMILES: O=c1c(O)c(-c2ccc(O)c(O)c2)oc2cc(O)cc(O)c12]

The presence or absence of caffeic or chlorogenic acids, coumarin, alkaloids, glycosylated flavonoids or aglycones, in grass pollens, was assessed using Thin Layer Chromatography (TLC). Briefly, grass pollen raw materials or extracts were processed using organic solvents (hexane, methanol . . . ) and were allowed to migrate into a silica gel in a solvent mixture specific for the compound to be tested.

No chlorogenic, caffeic acid coumarin or alkaloid could be found in a 5 grass pollen mix.

As regards flavonoids, bands were observed in every single grass pollen species using a protocol aimed at detecting flavonoid glycosides. Conversely, flavonoid aglycones could not be found in grass pollen using the appropriate protocol.

Accordingly, among all the assayed substances or substance groups known to possess a genotoxic potential in vitro, only flavonoids were found in grass pollens. More specifically, flavonoids found in grass pollens were flavonoid glycosides only, as no flavonoid aglycones could be detected. This is consistent with published data since the most common flavonoids isolated from pollen are flavonoid glycosides whereas aglycones do not occur naturally in pollen (Mo Y, Nagel C, Taylor L P. Proc. Natl. Acad. Sci. USA. 1992; 89: 7213-7217; Campos M G, Webby R F, Markham K R. Z. Naturforsch. [C]. 2002; 57: 944-946).

Example 4

Explanation for the In Vitro Genotoxic Potential of Grass Pollen Extracts by the Intrinsic Flavonoids 4.1. Working Hypothesis and Scientific Approach In view of the above findings, it was concluded that the genotoxic potential of grass pollen extracts must be associated with intrinsic flavonoids. However, no in vitro genotoxicity was reported for flavonoid glycosides, which are contained in the pollen extracts, whereas flavonoid aglycones, which were undetectable in the extracts, are known to display a genotoxic potential in vitro (Antognoni F, Ovidi E, Taddei A R, Gambellini G, Speranza A. Ahern. Lab. Anim. 2004; 32: 79-90; Nagao M, Morita N, Yahagi T, Shimizu M, Kuroyanagi M, Fukuoka M, Yoshihira K, Natori S, Fujino T, Sugimura T. Environ. Mutagen. 1981; 3: 401-419; Brown J P. Mutat. Res. 1980; 75: 243-277).

As an enzyme capable of deglycosylating a flavonoid glycoside into its aglycone counterpart has been described in a pollen model (Taylor L P, Strenge D, Miller K D. The role of glycosylation in flavonol-induced pollen germination. Adv. Exp. Med. Biol. 1998; 439: 35-44), the hypothesis: was made that the in vitro genotoxic potential observed with grass pollen extracts would be due to deglycosylation of non-genotoxic flavonoid glycosides into in vitro genotoxic flavonoid aglycones by specific enzyme(s), both the flavonoid glycosides and the enzyme(s) being extractable from the pollens.

To demonstrate this working hypothesis, it was investigated whether:
  grass pollen flavonoids are identifiable as flavonoid glycosides only present in quantifiable amounts,
  those flavonoid glycosides are deglycosylated into flavonoid aglycones under the conditions of the 24-h long term protocol but not of the 3-h short term protocols of the MLA/TK test,
  the amounts of flavonoid aglycones released under such conditions are consistent with the results of the MLA/TK test obtained with the freeze-dried extracts of grass pollens.

4.2. Identification of Grass Pollen Flavonoids by Reverse Phase HPLC and HCl-Hydrolysis/Reverse Phase HPLC Grass pollen flavonoids were first identified by reverse phase HPLC, according to their hydrophobicity. Reverse phase HPLC was performed on a Atlantis dC18 column, 4.6×250 mm, 5 µm, Waters, Milford, Mass., USA; with a gradient elution: 0.1% formic acid qsp water to 0.1% formic acid qsp acetonitrile in 30 min; flow rate: 1 mL/min; run time: 45 min; detection wavelength: 354 or 254 nm; injection volume 50 µL. Importantly, grass pollen extracts were diluted 5 times in methanol before analysis in order to solubilize both flavonoid glycosides and flavonoid aglycones, the latter being hardly soluble in water.

HCl-hydrolysis prior to reverse phase HPLC analysis was also used since hydrolysis of flavonoid glycosides leads to deglycosylation. HPLC analysis of the deglycosylated molecules then allows identifying their aglycone moieties. For HCl-hydrolysis, flavonoids of a grass pollen crude extract were first purified on Amberlite XAD-2, a resin currently used for flavonoid isolation (Gil M I, Ferreres F, Francisco A. Tomás-Barberán F A. J. Agric. Food Chem. 1998; 46: 2007-2012; D'Arcy B R. Antioxidants in Australian floral honeys: Identification of health-enhancing nutrient components: a report for the Rural Industries Research and Development Corporation. D'Arcy B R, Barton, A. C. T.: Rural Industries Research and Development Corporation, 2005, 84 p). Flavonoid aglycone and flavonoid glycoside standards were purchased from Extrasynthese (Genay, France).

Reverse phase HPLC indicated that an extract of 5 grass pollens contain: 1. a majority of highly polar flavonoids, appearing as peaks n° 1 and n° 2 2. small amounts of moderately polar flavonoids, appearing as peaks n° 3, 4 and 5 3. no detectable flavonoid aglycones. Retention times were as follows: peak n° 1 14.975, peak n° 2 15.151, peak n° 3 15.449, peak n° 4 16.022, peak n° 5 16.365, peak n° 6 17.117 (absorbance at 354 nm).

Based on the peaks area, peaks n° 1 and n° 2 represent more than 90% of the overall detected flavonoids within grass pollen. As a consequence identification was focused on the components of peaks n° 1 and 2.

According to their RT, the main flavonoids of grass pollen extract (peaks n° 1 and n° 2) were probably flavonoid diglycosides. However, because the observed RT did not correspond to any of the flavonoid standards we tested (flavone, rhamnetin, isorhamnetin, kaempferol, quercetin, quercetin-4'-O-glucoside, isorhamnetin-3-O-glucoside, kaempferol-3-O-glucoside, quercetin-3-O-galactoside, quercetin-3-O-glucoside, kaempferol-3-O-glucorhamnoside, quercetin-3-O-glucorhamnoside, kaempferol-3-O-robinoside-7-O-rhamnoside), the main flavonoids of grass pollen extracts could not be identified at this stage.

In order to determine the aglycone moieties of the grass pollen flavonoid glycosides, a deglycosylation was performed by HCl-hydrolysis of flavonoids purified from a grass pollen crude extract. HCl-hydrolysis released quercetin, kaempferol and isorhamnetin. Thus, the flavonoids of grass pollen extracts were glycosylated forms of quercetin, kaempferol and isorhamnetin.

Assuming that the peak areas obtained for quercetin, kaempferol and isorhamnetin are representative of their relative concentrations, the flavonoid aglycones produced by HCl-hydrolysis of a grass pollen extract are composed of 18% quercetin, 5% kaempferol and 77% isorhamnetin.

4.3. Further Identification of Grass Pollen Flavonoids by Mass Spectrometry Analysis Prior to mass spectrometry analysis, flavonoids of grass pollen extracts were separated using the HPLC method described above and manually collected from the HPLC column. Mass spectrometry analyses were performed using electrospray ionization-tandem mass spectrometry (ESI-MS/MS) in negative ion mode on a ThermoElectron LCQ Duo ion-trap mass spectrometer (San Jose, Calif., USA), after direct infusion of the samples. Fragmentation was obtained by collision-induced dissociation with helium.

According to data obtained from commercially available standards, mass spectra of flavonoid glycosides are easily interpretable: electrospray fragmentation leads mainly to the loss of part or all of their glycoside moiety(ies). Most particularly, all tested flavonoid glucosides (kaempferol-3-O-glucoside, quercetin-3-O-glucoside, isorhamnetin-3-O-glucoside, quercetin-3-O-glucorhamnoside, and kaempferol-3-O-robinoside-7-O-rhamnoside) loose a 120-Dalton part of the glucose or the whole 163-Dalton glucose moiety during fragmentation.

The two main peaks resolved in the HPLC method were analyzed by mass spectrometry analysis:

1. Peak n° 2 with a Mean Retention Time of 15.00 min:

One single ion appeared as a major parent ion, at m/z 639, therefore corresponding to a molecule of a 640-Da mass, referred to as "[M]". A minor parent ion was observed at m/z 1279, most likely corresponding to a [2M-H]—negative dimer ion of the 640-Da molecule ("H" standing for "1 hydrogen atom").

Cocksfoot and timothy grass pollens were described to contain a 640-Da flavonoid diglycoside, namely isorhamnetin-3,4'-diglucoside (Inglett G E. Nature 1956; 178: 1346. Inglett G E. J. Org. Chem. 1957; 22: 189-192), also found in other pollens such as the one of Crocus (Kuhn R, Löw I. Chem. Ber. 1944; 77: 196-202). Since the fragmentation spectrum obtained for the 15.00 min-HPLC peak can be easily interpreted as a the one of isorhamnetin-3,4'-diglucoside, it was concluded that the component of the major HPLC peak n° 2 corresponds to isorhamnetin-3,4'-diglucoside.

2. Peak n° 1 with a Mean Retention Time of 14.83 min:

According to mass spectrometry analysis in negative ion mode, four ions appeared as major parent ions: at m/z 639, 625, 609 and 463, therefore corresponding to 640-Da, 626-Da, 610-Da and 464-Da molecules, respectively. According to fragmentation analysis, the 640-Da molecule was isorhamnetin-diglucoside of peak n° 2 that contaminated peak n° 1.

Fragmentation spectra of parent ions at m/z 625 and 609 can be easily interpreted as the ones of quercetin-diglucoside and kaempferol-diglucoside, respectively. Assuming that both flavonoid glycosides are produced through the same metabolism as isorhamnetin-3,4'-diglucoside, and that they will be deglycosylated by the same specific enzymatic machinery, it was concluded that they are quercetin-3,4'-diglucoside (m=626 Da) and kaempferol-3,4'-diglucoside (m=610 Da), respectively.

Kaempferol-3,4'-diglucoside has already been described in pollen, namely in pollen of *Trillium* species (Yoshitama K, Tominaga T, Kanemaru Y, Yahara S. XVI Internationl Botanical Congress, Abstract n° 2539). Quercetin-3,4'-diglucoside has also been described in plants, namely in onion (Bonaccorsi P, Caristi C, Gargiulli C, Leuzzi U. J. Agric. Food Chem. 2005; 53: 2733-2740; Mullen W, Crozier A. J. Oil Palm Res. 2006; *Special Issue (April)*: 65-80). However, to our knowledge this is the first time quercetin-3,4'-diglucoside is described in pollens.

According to its molecular mass, the 464-Da molecule might be quercetin-monoglycoside. This is confirmed by the fragment ion at m/z 301, corresponding to quercetin. The presence of quercetin-monoglycoside in peak n° 1 is surprising, as standard quercetin-monoglycosides display longer retention. Quercetin-monoglycoside of peak n° 1 might be complexed to other components of this peak, thus sharing the same retention time. It might also be produced by alteration of peak n° 1's quercetin-diglucoside during the purification steps. Anyhow, according to the mass spectrum this component of peak n° 1 is quantitatively less important than quercetin- and kaempferol-diglucoside.

Altogether, it was thus found that the extracts of 5 grass pollens contain the main following flavonoid glycosides, found in decreasing amounts: isorhamnetin-diglucoside, quercetin-diglucoside, kaempferol-diglucoside.

4.4 Quantification of Isorhamnetin-, Quercetin- and Kaempferol-Glycosides in Freeze-Dried Extracts of 5 Grass Pollens by HPLC-DAD After HCl-Hydrolysis Since no standard is available for isorhamnetin-, quercetin- and kaempferol-diglucosides, those flavonoids were quantified after HCl-hydrolysis. This induces deglycosylation into isorhamnetin, quercetin and kaempferol (aglycones) for which standard do exist. Knowing the molecular masses of both the aglycones and the diglucosides, the concentration of the latters can easily be deduced from the corresponding formers' concentrations.

Quantification of isorhamnetin, quercetin and kaempferol obtained after HCl-hydrolysis was performed by HPLC-DAD. In this method, the flavonoid aglycones are separated by HPLC and detection is performed using a diode-array detector (or DAD). This allows recording the absorption spectrum in the ultraviolet range. Given that two flavonoid aglycones do not share the same absorption spectra, HPLC-DAD allows the identification of a flavonoid aglycone on the basis of both its retention time and its absorption spectrum, by comparison with the corresponding standard molecule. Knowing the ratios between the molecular masses of the diglucosides and the aglycones, the concentration of isorhamnetin-, quercetin- and kaempferol-diglucosides can be easily deduced from the measured concentration of their aglycone counterparts.

Three batches of freeze-dried extracts of 5 grass pollens obtained using the non-optimized ultrafiltration step were quantified for isorhamnetin-, quercetin- and kaempferol-diglucosides after they were transformed into their aglycones by HCl-hydrolysis.

TABLE 2

Concentration of isorhamnetin, quercetin and kaempferol in three batches of sieved extract of 5 grass pollens, as measured by HPLC-DAD after HCl-hydrolysis, and deduced concentration of their respective diglucoside counterparts (in µg/mg)

| | concentration of flavonoid aglycones | | | | deduced concentration of flavonoid diglucosides | | | |
|---|---|---|---|---|---|---|---|---|
| batch n° | isorhamnetin (316 Da) | Quercetin (302 Da) | kaempferol (286 Da) | total flavonoid aglycones | isorhamnetin diglucoside (640 Da) | quercetin diglucoside (626 Da) | kaempferol diglucoside (610 Da) | total flavonoid diglucosides |
| 50299 | 1.70 | 0.34 | 0.10 | 2.14 | 3.44 | 0.70 | 0.21 | 4.36 |
| 50300 | 1.00 | 0.26 | 0.08 | 1.34 | 2.03 | 0.54 | 0.17 | 2.73 |
| 50311 | 1.30 | 0.35 | 0.09 | 1.74 | 2.63 | 0.73 | 0.19 | 3.55 |
| Mean | 1.33 | 0.32 | 0.09 | 1.74 | 2.70 | 0.66 | 0.19 | 3.55 |
| % | 77 | 18 | 5 | 100 | 76 | 19 | 5 | 100 |

The mean relative amounts of isorhamnetin, quercetin and kaempferol found after HCl-hydrolysis of grass pollen freeze-dried extracts are exactly the same as the ones estimated after HCl-hydrolysis of purified flavonoids of a crude pollen extract that is: 77% isorhamnetin, 18% quercetin and 5% kaempferol. These results confirm that, on a quantitative basis, grass pollen flavonoids are in the following order, from most to less abundant: isorhamnetin diglucoside, quercetin diglucoside, kaempferol diglucoside.

Overall, the freeze-dried extracts of 5 grass pollens obtained using the non-optimized ultrafiltration step contain 0.36% (w/w) of flavonoid diglucosides.

4.5 Deglycosylation of Grass Pollen Flavonoid Glycosides Under the Conditions of the 24-h Protocol but not of the 3-h Protocols of the MLA/TK Test The short term and long term protocols of the MLA/TK test involves incubation for 3 h at 37° C. and incubation for 24 h at 37° C., respectively. To demonstrate that flavonoid glycosides of grass pollens are deglycosylated in the conditions of the long term protocol but not of the short terms protocols of the MLA/TK test, a crude extract of grass pollen was placed at 37° C. and then sampled after 3 h and 24 h incubations. Samples were kept frozen until analyzed for their contents in flavonoid glycosides and flavonoid aglycones.

To demonstrate that deglycosylation was due to an active enzyme-dependent process, grass pollen flavonoids were separated from grass pollen proteins by purification on Amberlite XAD-2 resin (Gil M I, Ferreres F, Francisco A. Tomás-Barberán F A. J. Agric. Food Chem. 1998; 46: 2007-2012; D'Arcy B R. D'Arcy B R, Barton, A. C. T.: Rural Industries Research and Development Corporation, 2005, 84 p) and then analyzed before and after a 24-h incubation at 37° C.

Analysis of samples was performed using the HPLC method described above for the detection of flavonoids.

Incubation of a grass pollen extract at 37° C. induces a slight but detectable decrease in levels of flavonoid diglucosides (peaks with RT 14.98-min and 15.16 min-min retention times) as soon as after 3 h. After 3 h, however, appearance of the aglycones quercetin (RT=20.2 min) and isorhamnetin (RT=22.2 min) remains negligible, whereas no kaempferol (RT=22.0) could be detected. In fact, the decrease in flavonoid diglucosides mainly corresponds to a ~2-fold increase of two peaks' surfaces, with 16.4-min and 17.1-min retention times, respectively. A 16.4-min RT corresponds to quercetin monoglucoside and a 17.1-min RT corresponds to both kaempferol- and isorhamnetin-monoglucosides. Therefore, the increase of the two peaks is most likely a consequence of a partial deglycosylation of flavonoid-diglucosides into flavonoid-monoglucosides.

Extending the 37° C.-incubation to 24 h leads to a marked decrease of flavonoid diglucosides, a marked increase of flavonoid monoglucosides, a dramatic increase of the flavonoid aglycones quercetin, kaempferol and isorhamnetin (FIG. 1).

In return, when flavonoid glycosides isolated from a grass pollen extract were incubated for 24-h at 37° C., no change in the HPLC profile was observed. Since the isolated flavonoids did not contain any detectable protein according to an SDS-PAGE experiment, this confirmed that the phenomenon observed with a whole pollen extract is an enzyme-driven deglycosylation of flavonoid glycosides.

As (a) the sum of all peaks areas was rather well conserved and (b) the decrease of a flavonoid diglucoside-corresponding peak was related to the increase or appearance of flavonoid monoglycoside and/or aglycone-corresponding peak(s), it could be considered that the ratio between the two peaks areas is equivalent to the molar ratio of the corresponding flavonoids. On this basis, the decrease in quercetin-diglucoside leaded to an equal increase in molecules of quercetin-monoglucoside and in molecules of quercetin aglycone.

Based on the peaks areas, the decrease in flavonoid diglucosides after a 24-h incubation at 37° C. was in the order of ~40%. Since about half of the quercetin-diglucoside was transformed into quercetin aglycone, this means that ~20% of quercetin-diglucoside was transformed into quercetin (aglycone) under the conditions of the 24 h-long term protocol of the MLA/TK test.

Altogether, those results indicate that:
deglycosylation of grass pollen flavonoid diglucosides into flavonoid aglycones occurs under the conditions of the 24-h long term protocol of the MLA/TK test,
such a complete deglycosylation hardly occurs in the conditions of the 3-h short term protocols of the MLA/TK test,
the deglycosylation of flavonoid glycosides is driven by grass pollen extractable enzymes.

Most particularly, ~20% of grass pollen quercetin-diglucoside is transformed into quercetin (aglycone).

4.6. Consistency of the Amounts of Flavonoid Aglycones Released in the Conditions of the 24-h Long Term Protocol of the MLA/TK Test with Results from this Test To our knowledge, quercetin is the only flavonoid aglycone that was studied in the MLA/TK test, namely in a work by Meltz and MacGregor who used a 4-h short term protocol (Mutat. Res. 1981; 88: 317-324). On the other hand, it was proved to be the most genotoxic flavonoid aglycone by other in vitro genotoxic tests (Nagao M, Morita N, Yahagi T, Shimizu M, Kuroyanagi M, Fukuoka M, Yoshihira K, Natori S, Fujino T, Sugimura T. Environ. Mutagen. 1981; 3: 401-419; Brown J P. Mutat. Res. 1980; 75: 243-277; Czeczot H, Tudek B, Kusztelak J, Szymczyk T, Dobrowolska B, Glinkowska G, Malinowski J, Strzelecka H. Mutat. Res. 1990; 240: 209-216MacGregor J T, Jurd L. Mutat. Res. 1978; 54: 297-309).

Therefore, on the basis of the study by Meltz and MacGregor, it was determined whether the deglycosylation of grass pollen quercetin-diglucoside into quercetin aglycone could by itself explain the results of the MLA/TK test obtained with the freeze-dried extracts of grass pollen.

The amounts of quercetin released during the 24-h/S9-MLA/TK test was calculated on the basis of: the mean concentration of quercetin-diglucoside in freeze-dried extracts, as determined above; and the level of deglycosylation of this molecule into quercetin aglycone in the conditions of this protocol, as also determined above.

The induction ratios that should result from those amounts was deduced from the data of Meltz and MacGregor. Such deduced induction ratios were then compared to the induction ratio actually observed.

It has been shown above that:
freeze-dried extracts obtained using the non-optimized ultrafiltration step contain on average of 0.32 μg/mg of quercetin in the form of flavonoid glycosides, mostly quercetin diglucoside;
~20% of quercetin diglucoside is deglycosylated into quercetin aglycone under the conditions of the 24-h long term of the MLA/TK test.

The concentrations of freeze-dried extracts tested in the 24-h/S9-protocol of MLA/TK were 13.5 mg/mL or below. The corresponding concentrations of released quercetin were then 0.864 μg/mL (20%×0.32 μg/mg×13.5 mg/mL) or below.

The lowest concentration of quercetin tested by Meltz and MacGregor was 10 μg/mL. Therefore, to determine the ratio that should be obtained with the lowest concentration of 0.864 μg/mL or below, the relationship between (a) the concentrations of quercetin tested by Meltz and MacGregor and (b) the corresponding induction ratios they observed was mathematically modelled. Since those ratios started reaching a plateau at the first concentration tested, we choose to use a logarithmic function for such a modelization. Given that the ratio is necessarily of 1 for 0 μg/mL of mutagen (control), the logarithmic function will be of the form:

$$y = a \cdot \ln(x+1) + 1 \qquad (1)$$

where y is the induction ratio, x is the concentration of quercetin and a is a constant number.

Indeed, according to equation (1), the induction ratio y is of 1 for a quercetin concentration x of 0.

Using the ratios obtained by Meltz and MacGregor for 10, 20 and 30 μg/mL of quercetin allows a mathematical modelization by the following equation with an excellent correlation coefficient (r=0.99):

$$y = 3.0822 \times \ln(x+1) + 1 \qquad (2).$$

Two freeze-dried extracts obtained using the non-optimized ultrafiltration step were studied in the 24-h/S9-MLA/TK test, namely: batch n° 40244 and batch n° 52494, which displayed a genotoxic potential at concentrations of 13.5 and 12.9 mg/mL, respectively. The corresponding concentration of quercetin released during the test is of 0.83-0.86 μg/mL (see above for calculation). According to equation (2) the induction ratio that should be obtained at this concentration is of 2.9 (2.86-2.91). The induction ratios obtained experimentally for batch n° 40244 and 52494 were of 2.1 and 3.5, respectively, that is, a mean of 2.8, which is virtually identical to the interpolated induction ratio of 2.9.

Since the induction ratio actually observed is identical to the induction ratio interpolated from the published data on the genotoxic potential of quercetin in MLA/TK test, we conclude that most, if not all, of the genotoxic potential of freeze-dried extracts of grass pollen obtained using the non-optimized ultrafiltration step can be explained by the production of quercetin through deglycosylation of quercetin-diglucoside during the test.

However, contribution of the deglycosylation of kaempferol- and isorhamnetin-diglucosides, albeit theoretically negligible, cannot be excluded.

4.7. Optimization of Ultrafiltration Step

The manufacturing process of grass pollen extracts involves ultrafiltration step with 2.5 volumes of washing with purified water on a 1 kDa-membrane.

Ultrafiltration step on a 1 kDa-membrane was compared with ultrafiltration step on a 5 kDa-membrane. Washings were performed with from 1 to 15 volumes of purified water. It was found that the cut-off value of the membrane had no impact of the immunoreactivity and protein content of the pollen allergen preparation. The volume of purified water for washing did neither influence the quality of the allergen preparation. It was concluded that ultrafiltration may be performed on a 5 kDa membrane with up to 15 volumes of water without altering the quality of the pollen extract.

However, clotting was observed afterwards upon filtration with a 0.22 μm filter.

To avoid this clotting, ultrafiltration with a solution containing 120 ppm ammoniac, equivalent to 0.56 g/L ammonium bicarbonate, was used for washing instead of purified water. No filtration clotting could be observed upon filtration with a 0.22 μm filter.

It was further checked that activity and protein content of the pollen extracts were unaltered by replacement of purified water with a 0.56 g/L ammonium bicarbonate solution for washings. No difference between the two washing solutions could be seen up to 15 volumes of washings. However, above 15 volumes of purified water, a decreased allergenic activity was detected whereas the ammonium bicarbonate solution was assayed up to 30 volumes of washing without detrimental effect of the allergenic activity of the pollen extract.

Flavonoid dosages indicated that washing with 2.5 volumes of purified water or ammonium bicarbonate 0.56 g/L enabled to remove about 80% of flavonoids. Flavonoids were completely removed by 15 volumes of purified water or ammonium bicarbonate 0.56 g/L. Washing with 30 volumes of ammonium bicarbonate 0.56 g/L did not improved any further flavonoid removal.

Ultrafiltration with 15 volumes of washing on a 5 kDa-membrane was selected for further characterisation.

4.8. Demonstration of the Elimination of the Grass Pollen Flavonoids by an Optimized Ultrafiltration Step The manufacturing process of grass pollen extracts has been optimized at the ultrafiltration step, involving 15 volumes of washing on a 5 kDa-membrane instead of the previously used 2.5 volumes of washing on a 1 kDa-membrane.

To determine whether this optimized process is able to completely eliminate flavonoids, the latter were assayed at different steps of the optimized ultrafiltration step, namely: just before ultrafiltration, that is, after the concentration step, after ultrafiltration with 2.5 volumes of washing, after ultrafiltration with 15 volumes of washing. This was performed using the HPLC method described above for this purpose.

Flavonoids were also assayed in three batches of sieved freeze-dried extracts obtained using the optimized ultrafiltration step, as compared to three batches obtained using the previous non-optimized process. The same HPLC method was used for this assay.

Finally, flavonoids were accurately quantified in three batches of sieved freeze-dried extract obtained using the optimized ultrafiltration step. Quantification was performed by HPLC-DAD after HCl-hydrolysis.

As opposed to the previous non-optimized manufacturing process of 5 grass pollens extracts, the optimized process leads to complete elimination of grass pollen flavonoids (FIG. 2).

This was confirmed with freeze-dried extracts obtained using the optimized ultrafiltration step, which contained no detectable flavonoids, as opposed to the freeze-dried extracts obtained through the previous non-optimized process.

Using HPLC-DAD after HCl-hydrolysis, flavonoids, as expressed in aglycone equivalents, were below the limit of quantification in sieved freeze-dried extracts of grass pollens, that is, below 0.003% (or g/100 g), leading to a total concentration of flavonoid diglucosides below 0.15 μg per 300 IR tablet (Table 3).

TABLE 3

Concentration of isorhamnetin, quercetin and kaempferol in three batches of sieved freeze-dried extract of 5 grass pollens (active substance) obtained using the optimized ultrafiltration step as measured by HPLC-DAD after HCl-hydrolysis, deduced concentration of their respective diglucoside counterparts and deduced concentration of all flavonoid diglucosides in a corresponding 300 IR tablet

| | concentration of flavonoid aglycones (in % or g/100 g) | | | | deduced concentration of flavonoid diglucosides (in % or g/100 g)* | | | | deduced concentration of flavonoid diglucosides in a 300 IR tablet (in μg)** |
|---|---|---|---|---|---|---|---|---|---|
| batch n° | isorhamnetin | quercetin | kaempferol | total flavonoid aglycones | isorhamnetin diglucoside | quercetin diglucoside | kaempferol diglucoside | total flavonoid diglucosides | total flavonoid diglucosides |
| 60099 | <0.001 | <0.001 | <0.001 | <0.003 | <0.002 | <0.002 | <0.002 | <0.006 | <0.15 |
| 60106 | <0.001 | <0.001 | <0.001 | <0.003 | <0.002 | <0.002 | <0.002 | <0.006 | <0.15 |
| 60113 | <0.001 | <0.001 | <0.001 | <0.003 | <0.002 | <0.002 | <0.002 | <0.006 | <0.15 |

Therefore, the optimized ultrafiltration step in the optimized manufacturing process resulted in a thorough removal of flavonoids from the extracts.

Conclusions

In our efforts to determine the intrinsic causes of the in vitro genotoxic potential of grass pollen extracts, the followings were demonstrated:

grass pollen extracts of 5 grass pollen contain flavonoid glycosides, mostly identified as quercetin-diglucoside, kaempferol-diglucoside and isorhamnetin diglucoside, under the conditions of the 24-h long term protocol of the MLA/TK test, grass pollen flavonoid glycosides are deglycosylated into their aglycone counterparts, namely: quercetin, kaempferol and isorhamnetin, most particularly, ~20% of quercetin diglucoside are transformed into quercetin (aglycone) in those conditions, on the basis of published data, the corresponding amounts of produced quercetin can totally explain the level of genotoxicity observed with the sieved freeze-dried extracts of 5 grass pollens obtained using the non-optimized ultrafiltration step, almost no flavonoid aglycones are obtained under the conditions of the 3-h short term protocols of the MLA/TK test, consistent with the absence of genotoxic potential under those conditions, extending the ultrafiltration step, as per the optimized ultrafiltration step, results in removal of flavonoids from the extracts to undetectable amounts.

Since external genotoxic contaminants were undetectable and/or largely below the calculated limit doses in grass pollen raw materials, the in vitro genotoxic potential of grass pollen extracts observed in the 24 h/S9-protocol of the MLA/TK test must be explained by grass pollen intrinsic substances. In this respect, it was demonstrated that the following mechanism occurs under the conditions of the assay: nongenotoxic flavonoid glycosides from grass pollens, namely isorhamnetin-diglucoside, quercetin-diglucoside and kaempferol-diglucoside, are deglycosylated by pollen-derived enzymes into their aglycone counterparts, namely isorhamnetin, quercetin and kaempferol, respectively, which are well-known to display a genotoxic potential in vitro, although they have never been proved genotoxic in vivo.

On the basis of published data on quercetin genotoxicity in the MLA/TK test, the amounts of quercetin released by grass pollen can totally explain the grass pollen in vitro genotoxic potential of grass pollen.

The theoretical risk associated with the presence of flavonoids in grass pollen extracts has been definitely eliminated by extending the ultrafiltration step of the manufacturing process, resulting in complete removal of pollen-derived flavonoids from the extracts. It was calculated that a daily administration of 300 IR tablets of grass pollen extract obtained using the optimized ultfiltration step would lead to a theoretical daily intake below 0.15 µg of pollen-derived flavonoids, well below the daily intake of flavonoids through common diet which is of 20 mg to 1 g.

The invention claimed is:

1. A method of reducing in vitro genotoxicity of a pollen extract which comprises reducing the amount of a flavonoid in the pollen extract by ultrafiltration of the pollen extract with at least 5 volumes of an ammonium bicarbonate solution, and then subjecting the ultrafiltered pollen extract, in an ammonium bicarbonate solution, to sterile filtration on a 0.22 µm filter.

2. The method according to claim 1, wherein said flavonoid is a flavonoid glycoside.

3. The method according to claim 1, wherein said flavonoid is at least one flavonoid glycoside selected from the group consisting of isorhamnetin-diglucoside, quercetin-diglucoside and kaempferol-diglucoside.

4. The method according to claim 1, wherein said pollen extract is an extract of a mixture consisting of, or comprising, cocksfoot, meadow-grass, lye-grass, sweet vernal-grass pollens.

5. A method of preparing purified allergen extract, which method comprises ultrafiltration of an aqueous allergen extract on a 1-10 kDa membrane with at least five volumes of an ammonium bicarbonate solution, and then subjecting the ultrafiltered allergen extract, in an ammonium bicarbonate solution, to sterile filtration on a 0.22 µm filter.

6. The method according to claim 5, wherein ultrafiltration of said aqueous allergen extract is performed on a 5-10 kDa membrane with 10 to 30 volumes of a 0.4 g/L to 0.8 g/L ammonium bicarbonate solution.

7. The method according to claim 5, wherein said allergen is selected from the group consisting of a tree pollen allergens, grass pollen allergens, herb pollen allergens, weed pollen allergens, mite allergens, venom allergens, animal hair and dandruff allergens, and food allergens.

8. The method according to claim 5, which further comprises the step of formulating said purified pollen extract into a pharmaceutical composition.

* * * * *